US009989551B2

(12) United States Patent
Wang et al.

(10) Patent No.: US 9,989,551 B2
(45) Date of Patent: Jun. 5, 2018

(54) REAL-TIME VOLUME CONFIRMATION DISPENSING APPARATUS AND METHODS

(71) Applicant: Siemens Healthcare Diagnostics Inc., Tarrytown, NY (US)

(72) Inventors: Litao Wang, Oakland, NJ (US); Pei-Ying Hsieh, Hillsdale, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 196 days.

(21) Appl. No.: 14/766,729

(22) PCT Filed: Feb. 14, 2014

(86) PCT No.: PCT/US2014/016564
§ 371 (c)(1),
(2) Date: Aug. 7, 2015

(87) PCT Pub. No.: WO2014/127277
PCT Pub. Date: Aug. 21, 2014

(65) Prior Publication Data
US 2016/0003860 A1 Jan. 7, 2016

Related U.S. Application Data

(60) Provisional application No. 61/765,087, filed on Feb. 15, 2013.

(51) Int. Cl.
*G01N 35/10* (2006.01)
*G01N 9/00* (2006.01)
*G01L 9/00* (2006.01)

(52) U.S. Cl.
CPC ............ *G01N 35/1016* (2013.01); *G01L 9/00* (2013.01); *G01N 2035/1018* (2013.01)

(58) Field of Classification Search
CPC ........ G01N 35/1016; G01N 2035/1018; G01L 9/00
See application file for complete search history.

(56) References Cited

U.S. PATENT DOCUMENTS 5,463,895 A 11/1995 Brentz
5,488,854 A * 2/1996 Kawanabe .............. G01F 23/14
73/19.05

(Continued)

FOREIGN PATENT DOCUMENTS

| EP | 1391734 A2 | 2/2004 |
| EP | 2246705 A1 | 11/2010 |
| WO | 2014/055590 A1 | 4/2014 |

OTHER PUBLICATIONS

PCT International Search Report and Written Opinion dated Jun. 3, 2014 (16 Pages).

(Continued)

*Primary Examiner* — Brian R Gordon

(57) ABSTRACT

A method of confirming volume during dispensing of a liquid using pressure. The method includes attempting to dispense a volume of the liquid from a dispense port, measuring a pressure associated with the attempted dispense of the liquid and providing a measured pressure signal, determining a liquid dispensing start time and a stop time based on a slope of the measured pressure signal, integrating the measured pressure signal between the start time and the stop time to provide an integrated pressure value, and comparing the integrated pressure value to one or more preset threshold values. Liquid dispensing apparatus are provided, as are other aspects.

15 Claims, 7 Drawing Sheets

(56) References Cited

U.S. PATENT DOCUMENTS

| | | | |
|---|---|---|---|
| 5,537,880 A * | 7/1996 | Takeda | G01M 3/26 73/40 |
| 5,540,081 A | 7/1996 | Takeda et al. | |
| 5,965,828 A * | 10/1999 | Merriam | G01F 11/00 137/557 |
| 6,022,747 A | 2/2000 | Gherson et al. | |
| 6,158,269 A | 12/2000 | Dorenkott et al. | |
| 6,322,752 B1 | 11/2001 | Siddiqui et al. | |
| 6,370,942 B1 * | 4/2002 | Dunfee | G01M 3/26 73/1.74 |
| 6,851,453 B2 | 2/2005 | Lipscomb et al. | |
| 7,477,997 B2 | 1/2009 | Kaplit | |
| 7,634,378 B2 | 12/2009 | Kaplit | |
| 7,792,647 B1 | 9/2010 | Ding et al. | |
| 7,804,599 B2 | 9/2010 | Calderoni | |
| 7,867,769 B2 | 1/2011 | Dunfee et al. | |
| 7,926,325 B2 | 4/2011 | Kaplit | |
| 2001/0047692 A1 * | 12/2001 | Lipscomb | G01N 35/1009 73/864.25 |
| 2003/0209093 A1 | 11/2003 | Lipscomb et al. | |
| 2004/0034479 A1 * | 2/2004 | Shimase | G01N 35/1016 702/19 |
| 2009/0007628 A1 * | 1/2009 | Johansson | B01L 3/021 73/1.74 |
| 2009/0070049 A1 * | 3/2009 | Ziegler | G01N 35/1016 702/50 |
| 2012/0226449 A1 | 9/2012 | Delache et al. | |

OTHER PUBLICATIONS

Honeywell Product Range Guide, Airflow, Force and Pressure Sensors. Dec. 2012, pp. 1-20 [online], [retrieved on May 15, 2014]. Retrieved from the internet <URL: http://sensing.honeywell.com/honeywell-sensing-pressue-force-flow-rangeguide-0080E1-15-en.pdf?name=26PCBFG2G>; p. 11.

Extended EP Search Report dated Sep. 14, 2016 of corresponding European Application No. 4751340.2, 4 Pages.

* cited by examiner

REAL-TIME VOLUME CONFIRMATION DISPENSING APPARATUS AND METHODS

RELATED APPLICATIONS

This application claims priority to U.S. Provisional Application Ser. No. 61/765,087 entitled "REAL-TIME VOLUME CONFIRMATION DISPENSING APPARATUS AND METHODS" filed on Feb. 15, 2013, the disclosure of which is hereby incorporated by reference in its entirety herein.

FIELD

The present invention relates generally to apparatus, systems, and methods adapted for dispensing liquids in diagnostic instruments.

BACKGROUND

In automated medical specimen diagnostic instruments (clinical analyzers and immunoassay instruments), patient biological specimens as well as reagents, acids, and bases may be dispensed. Some immunoassay systems may use a simple pressure measurement technique to verify a proper aspiration of the patient biological specimen. However, existing production immunoassay systems simply rely on the general reliability of the liquid delivery system to ensure integrity of acid and base additions. If there are small air bubbles in the liquid delivery line for the acid or base, this may not be detected.

Some existing systems utilize a capacitance sensing technique to confirm the liquid depth of the patient biological specimen, reagent, or combination of specimen and reagent. This capacitive probe technique requires a moving conductive probe, which touches a surface of the specimen, reagent, or combination. However, capacitance sensing is difficult, due to the possible existence of foaming on top of the liquid.

Accordingly, diagnostic instruments having improved ability to effectively verify liquid delivery are desired.

SUMMARY

According to a first embodiment, a method of detecting pressure during dispensing of a liquid, such as an acid or a base, is provided. The method includes attempting to dispense a volume of the liquid from a dispense port, measuring a pressure associated with the attempted dispense of the liquid and providing a measured pressure signal, determining a start time and a stop time based on a slope of the measured pressure signal, integrating the measured pressure signal between the start time and the stop time to provide an integrated pressure value; and comparing the integrated pressure value to one or more preset threshold values.

According to another aspect, a liquid dispensing apparatus is provided. The liquid dispensing apparatus includes a manifold having an input port configured to receive a liquid to be dispensed, an dispense port configured to dispense the liquid, a flow passage in the manifold, and a pressure port coupled to the flow passage, a pump coupled to the input port and configured to cause the liquid to flow in the flow passage, a pressure sensor coupled to the pressure port and adapted to measure a pressure during the dispense and provide a measured pressure signal, and a controller coupled to the pressure sensor and operational to: determine a start time and a stop time by taking a difference of the measured pressure signal over a time window, integrate the measured pressure signal between the start time and the stop time to provide an integrated pressure value, and compare the integrated pressure value to one or more preset threshold values.

According to another aspect, a liquid dispensing apparatus is provided. The liquid dispensing apparatus includes a manifold having an input port configured to receive a liquid comprising an acid or a base to be dispensed, an dispense port configured to dispense the acid or base, a flow passage in the manifold, and a pressure port coupled to the flow passage, a pump coupled to the input port and configured and adapted to cause the acid or base to flow in the flow passage, a pressure sensor coupled to the pressure port and adapted to measure a pressure during the dispense and provide a raw measured pressure signal, and a controller coupled to the pressure sensor and operational to: provide a measured pressure signal by subtracting a reference pressure signal from the raw measured pressure signal, determine a start time and a stop time by taking a difference of the measured pressure signal over a time window, integrate the measured pressure signal between the start time and the stop time to provide an integrated pressure value, and compare the integrated pressure value to preset upper threshold value and a preset lower threshold value.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

BRIEF DESCRIPTION OF THE DRAWINGS

The invention will be better understood by referring to the detailed description taken in conjunction with the following drawings.

DETAILED DESCRIPTION

Figure 1:
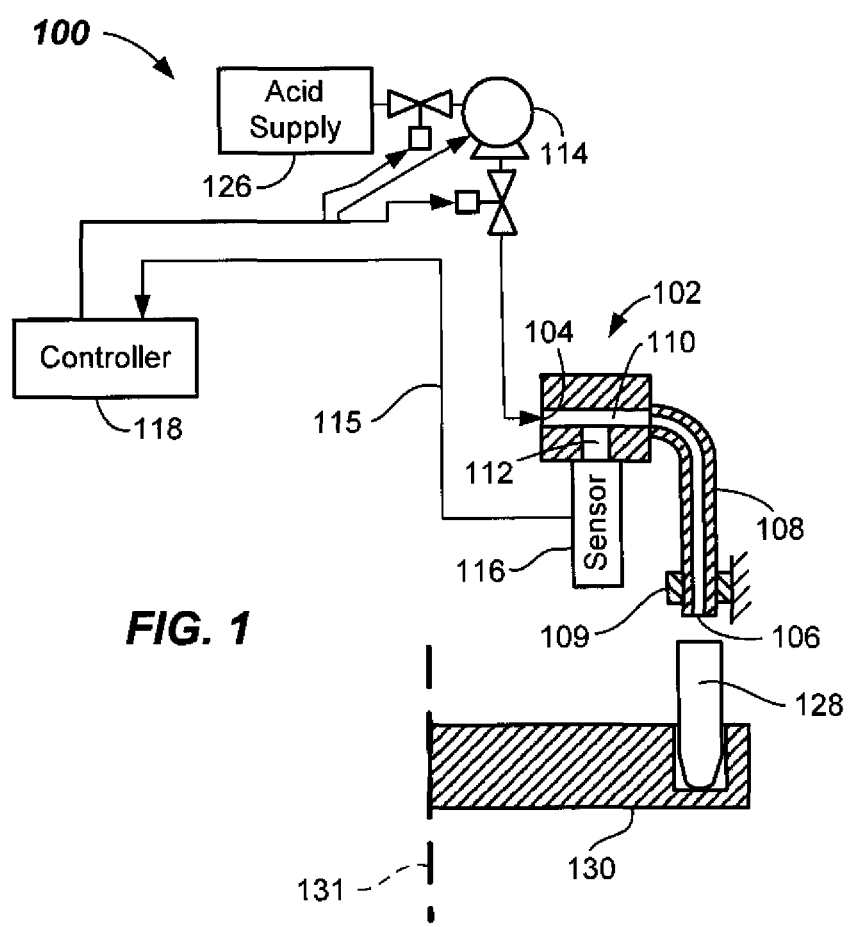
FIG. 1 illustrates a side schematic view of a liquid dispensing apparatus according to embodiments.

In diagnostic instruments, it may be desirable to independently confirm each dispense step of the immunoassay or testing process to ensure that no false clinical results are reported. Embodiments of the present invention provide apparatus and methods adapted and operational to provide confirmation of a liquid dispense, such as a dispense of an acid and/or a base. This may be in addition to confirming aspiration and/or dispense of the biological liquid specimen and any reagent. Addition of the acid and/or base dispense may increase confidence that a user may have in the clinical accuracy of the diagnostic instrument and results thereof.

Additionally, some diagnostic instruments may have constraints on the addition of a moving probe, especially during base addition, due to light tightness issues, i.e., the base addition is in the area of the light reading device (e.g., luminometer) and should be relatively light tight. Having a moving probe is difficult to implement in this light tight base addition environment.

Embodiments of the invention are beneficial to various diagnostic instruments by allowing, for example, verification of acid and/or base dispense operations. Accordingly, improved confidence in testing results may be achieved.

In accordance with one or more embodiments, apparatus and methods include a fluid-handling (e.g., fluidics) manifold with a pressure sensor mounted or connected thereto. The manifold is connected to the acid and/or base liquid delivery lines, and in one embodiment a separate manifold is connected to each of the acid and base delivery lines. The manifold may be placed at a position in the respective liquid delivery line that is less than one dispensed volume shot from a dispense port in the respective line. During the dispense of the acid and/or base, the liquids flowing adjacent to the pressure sensor create a pressure profile or trace (e.g., a plot of raw measured pressure over time). The magnitude of the measured pressure signal depends on the hydraulic system used, and the speed, acceleration and deceleration of the pump used during the dispense operation.

According to a method aspect, the raw measured pressure signal may be processed by first digitizing the raw measured pressure signal. The measured pressure signal may be normalized by subtracting a reference pressure signal to provide a measured pressure signal (a digitized signal trace). Actual liquid dispensing start and stop times are then determined from the measured pressure signal. The start and stop times may be determined by estimating and analyzing a slope of the measured pressure signal. Start and stop times may be based upon a differential over a short time window being outside of preset start and stop thresholds. The method then calculates an integrated pressure value between the start and stop times. The integrated pressure value is compared with one or more preset threshold values. Failure modes due to one or more air bubbles in the delivery line, system leaks, or valve failures may be flagged by the method.

These and other aspects and features of embodiments of the invention will be described with reference to FIGS. 1-10 herein.

The liquid dispensing apparatus 100 may be included in a diagnostic instrument, for example, such as a clinical analyzer or immunoassay apparatus. As shown in FIG. 1, a first embodiment of the liquid dispensing apparatus 100 is shown. Liquid dispensing apparatus 100 is adapted to dispense an acid liquid within the diagnostic instrument. However, the liquid dispensing apparatus 100 is equally adapted to dispensing a base liquid within a diagnostic instrument. The method described herein comprises dispensing the liquid (e.g., an acid and/or base liquid) into a suitable reaction vessel, such as a cuvette, and verifying or confirming the completeness of the resultant dispense.

Liquid dispensing apparatus 100 includes a manifold 102 having an input port 104 configured to receive a liquid (e.g., an acid) to be dispensed. The liquid dispensing apparatus 100 includes a dispense port 106 configured and adapted to dispense the liquid (e.g., acid or a base) into a reaction vessel 128, such as a cuvette. Reaction vessel 128 may be received in a suitable receptacle in a carrier 130, such as a carrier ring, that may be moveable (e.g., rotatable about an axis 131), for example. Any numbers of cuvettes 128 may be included in receptacles formed in the carrier 130. And may sequentially receive acid or base dispenses from the liquid dispensing apparatus 100. The dispense port 106 may be included at an end of a short section of tubing 108 (e.g., a flexible plastic tubing) coupled to the manifold 102, that may be held in a defined location in space at an acid addition location (or base addition location) by a support structure 109. A flow passage 110 is provided in the manifold 102, and a pressure port 112 is coupled to the flow passage 110. Flow passage and tubing together make up a liquid delivery line. The flow passage 110 and pressure port 112 may have a diameter between about 0.5 mm and 2 mm, for example. Other dimensions may be used.

In the liquid dispensing apparatus 100, a pump 114 is coupled to the input port 104 and configured to cause the liquid (e.g., acid or base) to flow in the flow passage 110 from a liquid supply (e.g., acid supply 126) during a liquid dispense. The pump 114 may be any suitable precision pump, such as a piston-type pump that may be driven by a stepper motor, for example. Other suitable pump types may be used. Pump 114 may be sized to dispense shots (shot defined herein as a single dispense volume of acid) of between about 0.2 ml and about 1 mL. Pump 114 may include valves located before and/or after in the liquid delivery line.

A pressure sensor 116 is coupled to the pressure port 112, and is configured and adapted to measure a raw pressure signal during the liquid dispense (e.g., acid dispense or base dispense) operation. Pressure sensor 116 may be any suitable pressure sensor adapted to be in contact with an acid (or base), and which is capable of providing a pressure signal of suitable strength. Pressure sensor 116 may be mounted on the manifold 102 between the input port 104 and dispense port 106, as shown in FIG. 1. Pressure sensor 116 that is chemically compatible with an acid (or a base) may be selected.

In the depicted embodiment, the pressure sensor 116 may be a stainless steel pressure sensor having an operating range of between about 0-15 psi. Other suitable pressure sensors may be used. In some embodiments, the liquid acid (or base) may touch the pressure sensor 116 or there may be a small air gap in the pressure port 112 that is coupled to the flow passage 110. If an air gap is used, the air gap size should be consistently the same size. In some embodiments, the manifold 102 should be mounted relatively close to the dispense port 106 in the liquid delivery line (e.g., within one volume shot). In some embodiments, an orientation of the pressure sensor 116 may be aligned and oriented so that a majority of air in the manifold 102 is moved out during initial priming with the acid (or base).

During the dispense, a raw pressure signal is provided in line 115 by the pressure sensor 116, and is provided to a controller 118. A measured pressure signal is obtained by subtracting off a reference pressure signal from a raw measured pressure signal within a digital microprocessor within the controller 118, for example. Other suitable electronics for filtering (e.g., anti-aliasing filters), amplifying, and converting (e.g., A/D converter) the raw pressure signal to a digitized signal form may be used. The reference pressure signal is a signal that is measured just before the dispensing operation starts. An example of a trace of the measured pressure signal according to an aspect of the invention is shown in FIG. 3.

The controller 118, which is coupled to the pressure sensor 116, is operational to carry out the processing of the raw pressure data received from the pressure sensor 116. Controller 118 may also carry out other operations, such as starting and stopping of the pump 114, opening and closing of one or more control valves, starting and stopping a drive motor of the carrier 130, controlling motions of one or more pipettes, and the like. Controller 118 may be any suitable device capable of carrying out the signal processing and may include a suitable microprocessor, memory, power supply and other suitable digital and/or analog electronics.

Figure 3:
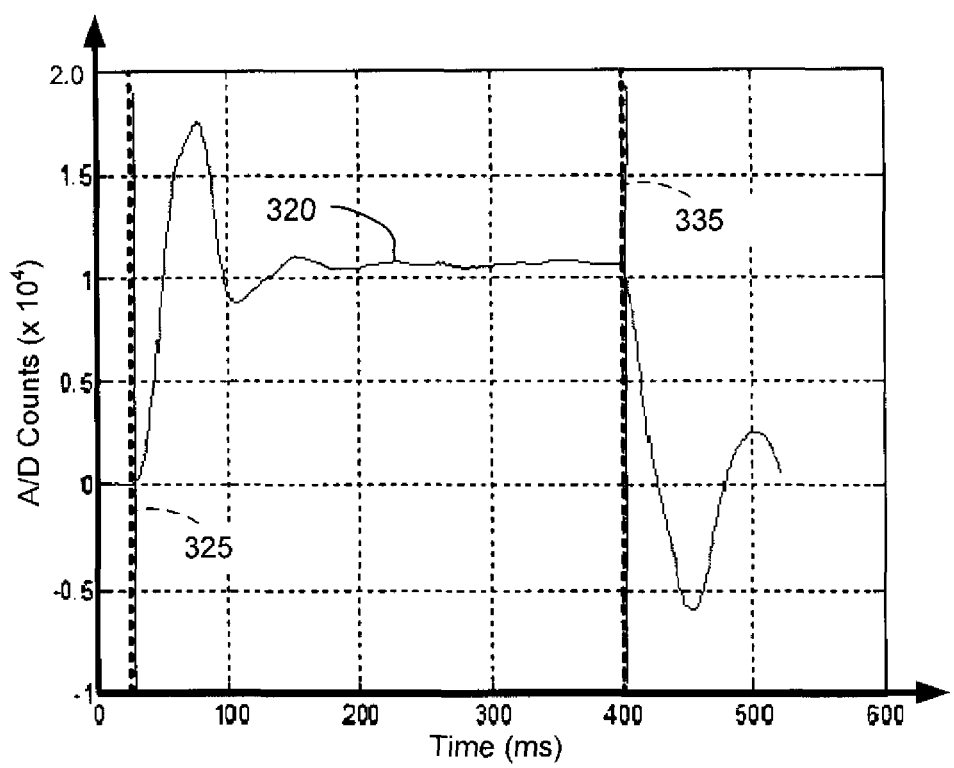
FIG. 3 illustrates a plot of a measured pressure signal versus time of a typical acid or base dispense according to embodiments.

In particular, the controller 118 is used to determine a (a liquid dispensing start time designated as 325 in FIG. 3) and a stop time (a liquid dispense stop time designated as 335 in FIG. 3). Start time 325 and stop time 335 may be determined by analyzing the slope measured pressure signal 320.

In one or more embodiments, start time 325 and stop time 335 are determined by monitoring the measured pressure signal 320 over a time range. In particular, an estimate of the slope of the measured pressure signal over the range may be determined and monitored. In one or more embodiments, the start time 325 and stop time 325 may be determined by taking a difference of the measured pressure signal over a short time window (e.g., between about 1 ms and 50 ms, or even between about 5 ms and 50 ms, or even between about 5 ms and 15 ms in some embodiments, for example). Other short time window lengths may be used. The differential pressure over this short time window is, in effect, a substitute for taking a first derivative.

In one or more other embodiments, start time 325 and stop time 335 may be determined by determining the slope by taking a derivative (e.g., a first derivative) of the measured pressure signal 320 over time during the dispensing. Other means for determining the start time and stop time based on slope may be used. For example, a rate of change of the slope may be used.

Figure 4:
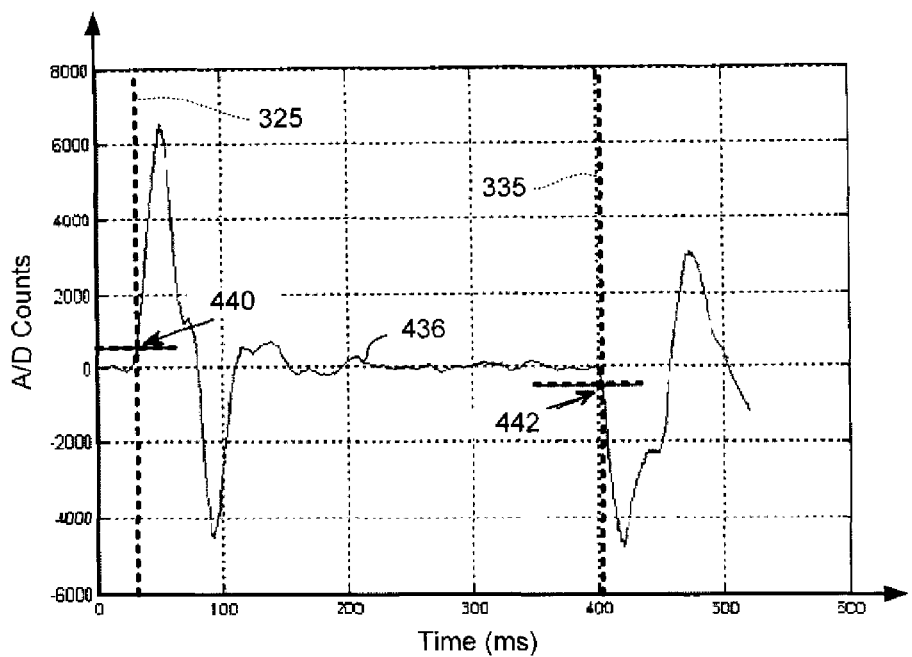
FIG. 4 illustrates a plot of a differential of the measured pressure signal over a short moving time window versus time of a typical acid or base dispense according to embodiments.

FIG. 4 shows the calculated differential pressure 436 over the time range of a single dispense shot of the liquid (e.g., acid or base), which is used to find the start time 325 and stop time 335. The horizontal lines represent a preset start threshold 440 and a preset stop threshold 442 that are used to determine when the pump 114 actually starts pumping liquid and stops pumping liquid instead of with air bubbles based upon the calculated differential pressure 436 (trace). The start time 325 is determined to be when the preset start threshold 440 is exceeded, and the stop time 335 is determined to be when the preset stop threshold 442 is exceeded (in the negative slope direction, typically below zero). The start and stop times 325, 335 are actually after the command to the pump 114 has been given by the controller. Accordingly, the present method provides a more accurate determination of when liquid actually flow starts and stops flowing in the liquid delivery line. The preset start threshold 440 and a preset stop threshold 442 may be determined experimentally, and should be far enough from zero so that they are not triggered by electrical signal noise and normal system variation.

Once the start time 325 is determined, the measured pressure signal 320 is integrated between the start time 325 until the stop time 335 is met (when the preset stop threshold 442 is exceeded in the negative slope direction). This integration provides an integrated pressure value (a number). Integration takes place using a suitable integrator in hardware and/or software operating within the controller 118. Once the integrated pressure value is determined, it may be compared to one or more preset integration threshold values that are stored in memory of the controller 118.

In some embodiments, a single preset threshold value (e.g., limit) setting of less than a predetermined (preset) integrated pressure threshold value is used. If the measured integrated pressure value for a dispense falls below the predetermined integrated pressure threshold value, then an abnormality in the dispense is flagged. This may be indicative of one or more air bubbles in the liquid delivery line, a system leak, or a valve failure, for example, depending on whether the threshold is set above or below the expected nominal integrated measured pressure value.

In another embodiment, both preset upper and lower threshold values are set. The upper and lower thresholds comprise an upper predetermined integrated pressure value, and also a lower predetermined integrated pressure threshold value. Thus, if the integrated measured pressure value falls inside the range between the upper and lower thresholds, a normal dispense is indicated. If the integrated measured pressure falls outside of the range (either above the upper threshold or below the lower threshold), then an abnormality in the dispense is flagged.

As discussed below, the range of the preset upper and lower threshold values may be less than +/−5% from a predetermined nominal integrated pressure value (an expected normal dispense value, which may be based on an average of multiple experimental tests), or even less than +/−2% from a predetermined nominal integrated pressure value in some embodiments. For example, the range may be set between about +/−1% and about +/−2% from a nominal (expected) integrated measured pressure value in one or more embodiments.

One example of a method of detecting and confirming pressure during dispensing of a liquid, such as a liquid acid or liquid base, will now be described. The acid and base volume dispense confirmation uses the measured pressure signal continuously sampled and collected while the liquid (acid or base) is being dispensed into the reaction cuvette 128 to verify proper dispensing. The measured pressure data (e.g., profile or trace) obtained from the sensor 116 of each volume dispense is then analyzed to confirm or flag the current dispensed volume. One example method used is described by the following:

1. The liquid dispensing apparatus 100 reads the reference pressure from the pressure sensor 116 just before the start of the liquid dispense. This is measured reference pressure is digitized and stored in memory of the controller 118.

2. The liquid dispensing apparatus 100 now reads the raw measured pressure signal from the pressure sensor 116 coupled to the manifold 102 continuously during the liquid dispense.

3. As the raw measured pressure signal is being digitized, the reference pressure is subtracted from each successive measurement of the raw measured pressure signal to provide the measure pressure signal 320. The measured pressure signal 320, being normalized, is shown as in FIG. 3.

4. Calculate an estimate of the instantaneous slope of the measured pressure signal 320. The estimate of the instantaneous slope may be provided by any suitable means. For example, a derivative (e.g., first derivative) may be calculated from the measured pressure signal. In some embodiments, estimating slope may be based on a differential pressure taken over a short time window, i.e., P(i+Window-Size)−P(i). A change (e.g., delta) in pressure over the short time window may be used as an estimate of slope (ΔP). The time window may be between about 1 ms and 50 ms, between about 5 ms and 50 ms, between about 5 ms and 15 ms, and may be about 10 ms in some embodiments.

5. The start time 325 may be determined to be when the slope estimate (e.g., first derivative or differential pressure) passes a preset start threshold 440 from the beginning of when the pump 114 was started.

6. The stop time 335 may be determined to be when the first derivative or a preset stop slope threshold 442 in the descending direction after the starting of the pump 114 is exceeded as shown in FIG. 4.

7. The measured pressure signal is then integrated between the pump start time 325 and pump stop time 335 to determine an integrated measured pressure value.

8. If the integrated measured pressure value is less than the preset lower threshold value 545, then this is indicative that there may be one or more air bubbles in the line, a system leak (e.g., leaking in the delivery line or a connection thereof), or a valve failure. If the integrated measured pressure is above a preset upper threshold value 550, then the liquid delivery line may be possibly clogged. Thus, in one or more embodiments, the method may detect a presence of a blockage in the liquid delivery line. If the integrated measured pressure value is outside the one or more preset threshold values 545, 550, then an alert is flagged, and/or the dispense is stopped. The alert may be a written warning, such as a written notice to an operator, an alarm, or a blinking light, for example. Other types of alerts may be used.

To determine the robustness of the dispense verification method, run-to-run variations, as well as within-the-run precision were evaluated under normal liquid dispensing conditions. A nominal dispensed volume of base was about 300 μL per dispense shot was used. The run-to-run variation of the averaged integrated pressure over 18 runs was less than ±1%. Each run had 20 replicates. The within-the-run precision (CV %) was less than 0.5%. In accordance with one or more embodiments, the lower threshold value 545 and upper threshold value 550 can be developed and set from this data. Based upon this limited data, threshold value limits of ±2% from a nominal integrated measured pressure value may be used. The threshold limits 545, 550 could be different for different applications. Acid volume dispense confirmation limits may be set in exactly the same manner as the base upper and lower threshold value limits.

In some embodiments, the integrated measured pressure thresholds for detecting air bubbles, system leaks, and/or valve failures may be selected in the range of (average of integrated pressure*(1+/−3*CV %)) to (average of integrated pressure*(1+/−10*CV %)), based on the statistical experience.

Figure 2:
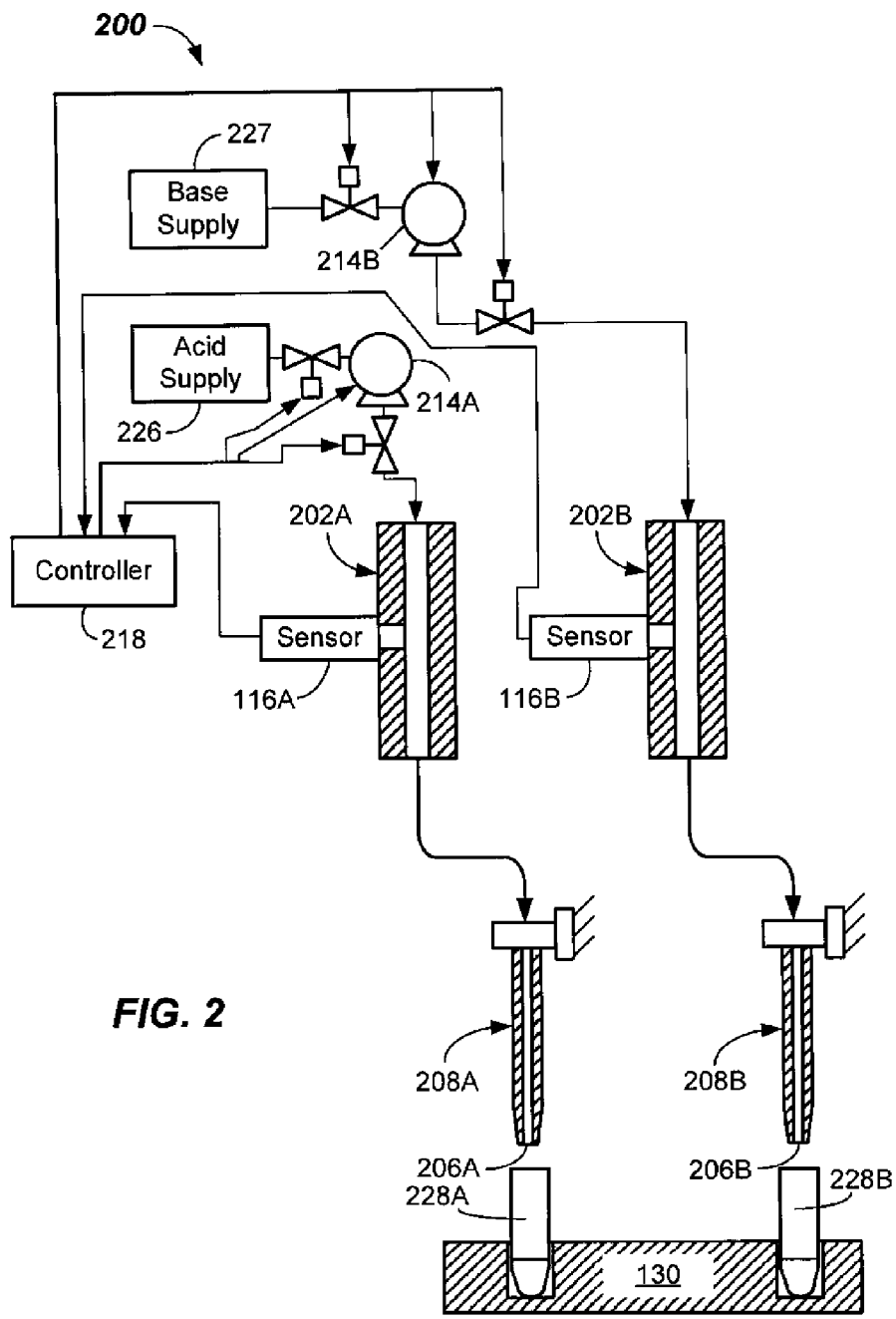
FIG. 2 illustrates a side schematic view of another liquid dispensing apparatus including both an acid and a base dispense according to embodiments.

FIG. 2 illustrates another embodiment of liquid dispense apparatus 200 configured and adapted to dispense and acid and a base and verify such dispenses according to embodiments. In the depicted embodiment, both the acid and base liquid delivery lines include manifolds 202A, 202B having pressure sensors 216A, 216B coupled thereto and adapted to provide raw measured pressure signals to the controller 218 during dispensing. The liquid acid and liquid base from the acid and base supplies 226, 227 are sequentially dispensed into the cuvettes 228A, 228B from the dispense ports 206A, 206B. As before described, pumps 214A, 214B may cause the dispensing through the manifolds 202A, 202B and tubing 208A, 208B. Other components may be as otherwise described in FIG. 1. Thus, the liquid dispense apparatus 200 can effectively verify acid and a base dispenses that follow the specimen and reagent additions to the cuvettes 228A, 228B.

In addition to verifying a normal dispense, the method was particularly evaluated to determine if it can properly flag air bubbles being present in the liquid delivery line, leaking, and/or valve failure. Base volume confirmation was used for a bubble verification study. However, it is believed that acid volume confirmation and bubble detection would operate exactly the same.

For the air bubble detection, some amount of air was introduced into the liquid delivery line from the base supply. As the air bubble moved up to the dispense port 106, the bubble was broken up into small bubbles.

Figure 5:
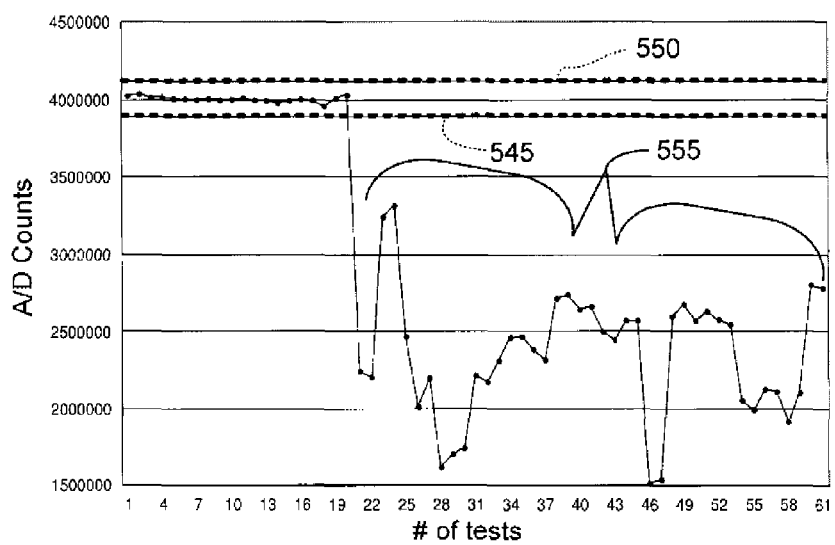
FIG. 5 illustrates a plot of the integrated pressure values for multiple runs of a base dispense; with the base dispense including air bubbles on the later runs according to embodiments.

FIG. 5 shows the integrated measured pressure values for the experimental air bubble testing for numerous test runs to be described below. The horizontal lines represent a lower integrated measured pressure threshold value 545 and an upper integrated measured pressure threshold value 550. The first 20 tests were from normal dispenses. The integrated pressure values of all the normal dispenses fall within the upper and lower integrated measured pressure threshold values 545, 550. The rest of the tests (labeled 555) were done with air bubbles in the liquid delivery line close to the manifold 102. As can be seen, all of the base dispenses with air bubbles present were properly flagged by the method, and determined by being outside (below) the lower integrated measured pressure threshold value 550.

Figure 6:
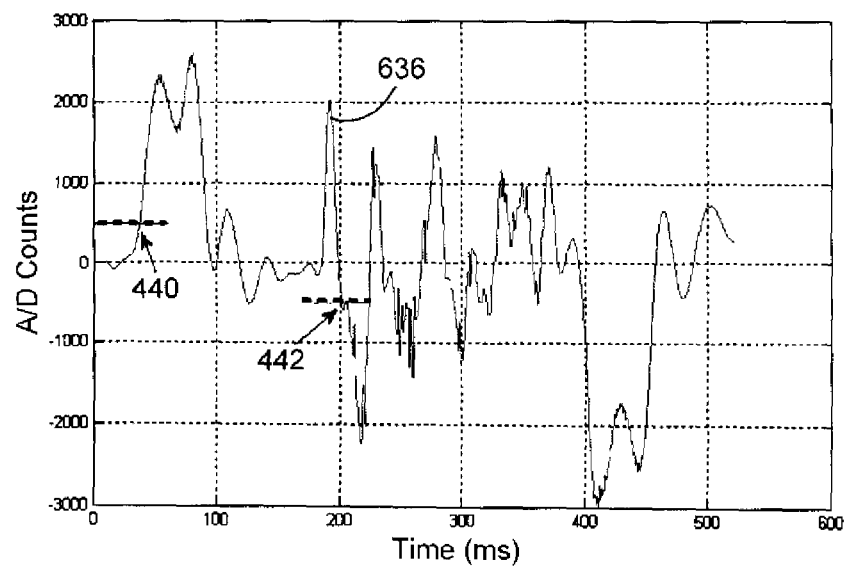
FIG. 6 illustrates a plot of a differential of the measured pressure signal over a short time window versus time of an acid or base dispense including one or more air bubbles according to embodiments.
Figure 7:
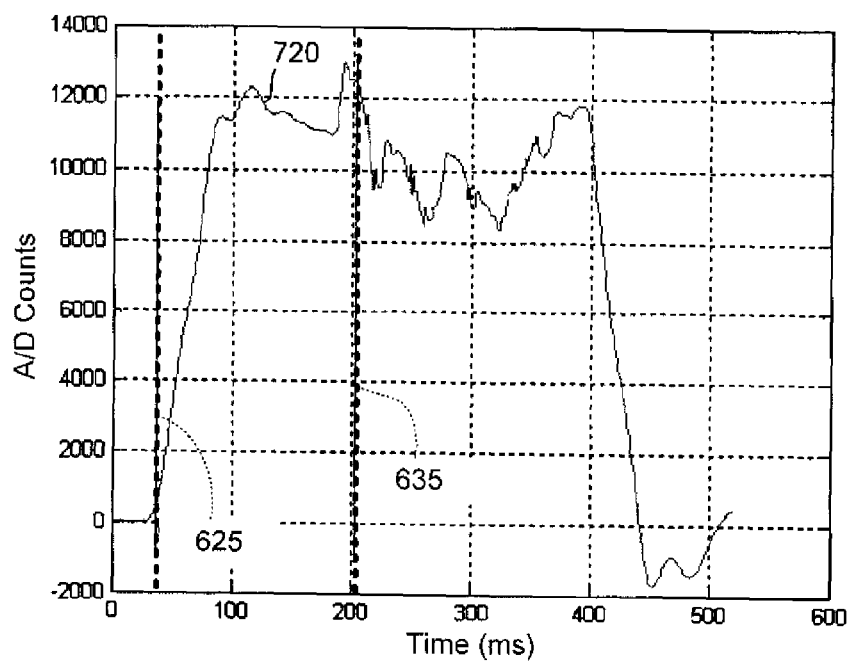
FIG. 7 illustrates a plot of the measured pressure signal versus time of an example of an acid or base dispense operation including one or more air bubbles according to embodiments.

FIGS. 6 and 7 illustrate example traces (pressure differential 636 and integrated pressure 720) of a liquid dispensing apparatus 100 having one or more air bubbles in the liquid delivery line. As can be seen, the start time 625 is flagged by the method, as is the stop time 635 via exceeding the start and stop threshold values 440, 442. However, the stop time 635 when the air bubbles start to pass the manifold occurs much sooner than is the case in a normal dispense run. As a result, as shown in FIG. 7, the time between the start time 625 and stop time 635 is reduced, resulting in a relatively lower integrated pressure value, which is flagged as air bubbles in the delivery lime when the integrated pressure value falls below the lower threshold limit 445.

Figure 8:
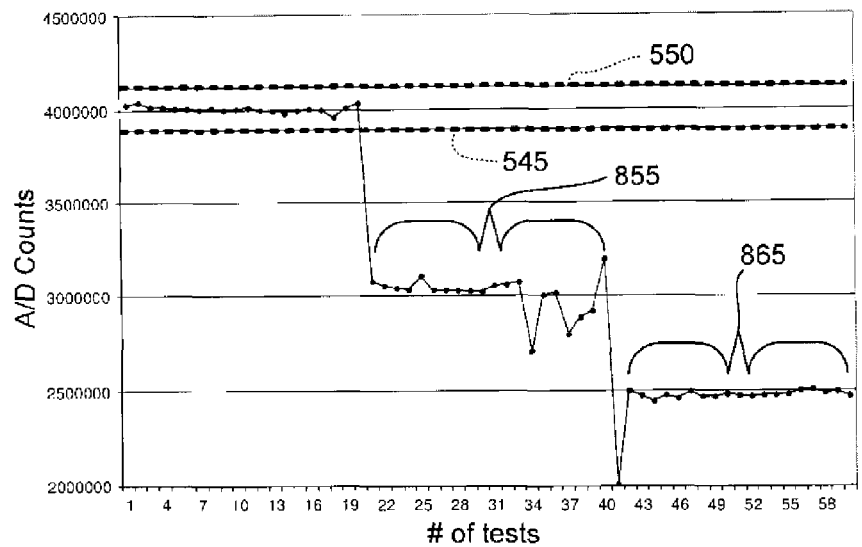
FIG. 8 illustrates a plot of an integrated measured pressure value for multiple runs of a base dispense including one or more system leaks according to embodiments.

Now referring to FIG. 8, to determine if the method may effectively flag system leaks, experimental system leak testing was performed. In the experimental system leak testing, micro-leaks were generated by loosening the tubing fittings slightly so that no obvious liquid dripping from the dispense port 106 was observed. The tubing fittings before the manifold 102 and after the manifold 102 were loosened. FIG. 8 shows the results of the system leak test. As before, the two horizontal lines represent the upper and lower integrated measured pressure threshold limits 545, 550. The first 20 tests were from normal runs, for comparison. They are within threshold limits 545, 550. The second 20 tests (labeled 855) and third 20 tests (labeled 865) were from systems with leaks before and after the manifold 102, respectively. All the tests having systems leaks from loosened fittings were flagged, in that the integrated measured pressure fell below the lower integrated measured pressure threshold limits 545.

Figure 9:
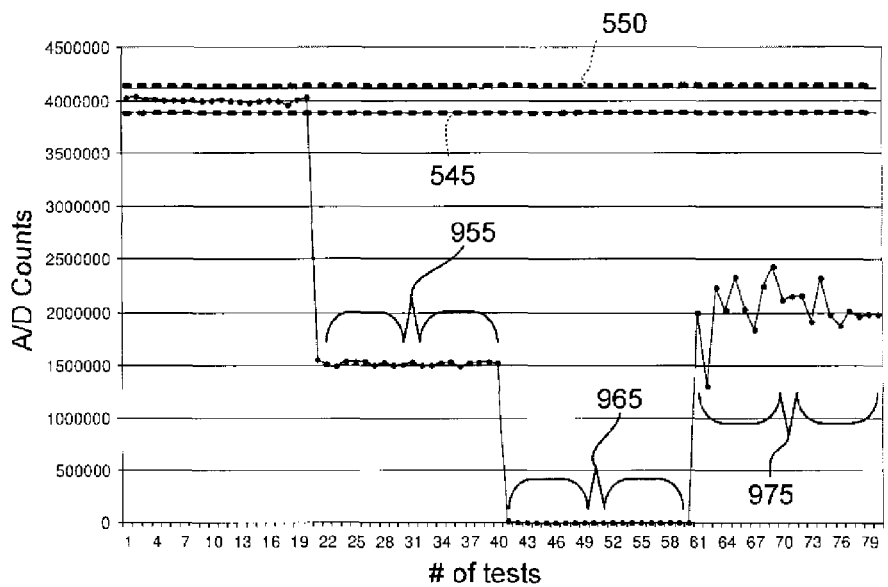
FIG. 9 illustrates a plot of an integrated measured pressure value for multiple runs of a base dispense including one or more valve failures according to embodiments.

Testing to determine if the method can effectively detect valve failures was also carried out. Valve failure was created with either the valve being stuck wide open or stuck closed. It is difficult to create test cases with the valve partially open or partially closed. However, in such a case, it should be similar as the system leak tests above. There are two valves in a typical acid or base liquid delivery apparatus 100. One valve is before the pump 114, and another valve is after the pump 114. The operation of each valve may be controllable by the controller 118. FIG. 9 shows the results of the valve failure tests. All the valve failure tests (except the first 20 tests which were normal runs, for comparison) were flagged by the method. The second 20 tests (labeled 955) and the third 20 tests (labeled 965) were from a stuck open valve before and after the pump 114, respectively. The last 20 tests (labeled 975) were from stuck closed valve before the pump 114. Except the second 20 tests (955), which only had very small amount of base dispensed, there were almost no liquid dispensed into cuvette 728 from the rest of tests.

As can be seen, the method flagged all system failure modes, which include air bubbles in the liquid delivery line, system leaks, and valve failures. Accordingly, the method is sufficient to confirm normal acid and base dispenses and flag abnormal dispenses. However, the present method in this invention can be used for any liquid delivery with proper stop time, start time, and integrated measured pressure threshold limits. All the tests having valve failures were flagged; in that the integrated measured pressures fell below the lower integrated measured pressure threshold limits 545.

Figure 10:
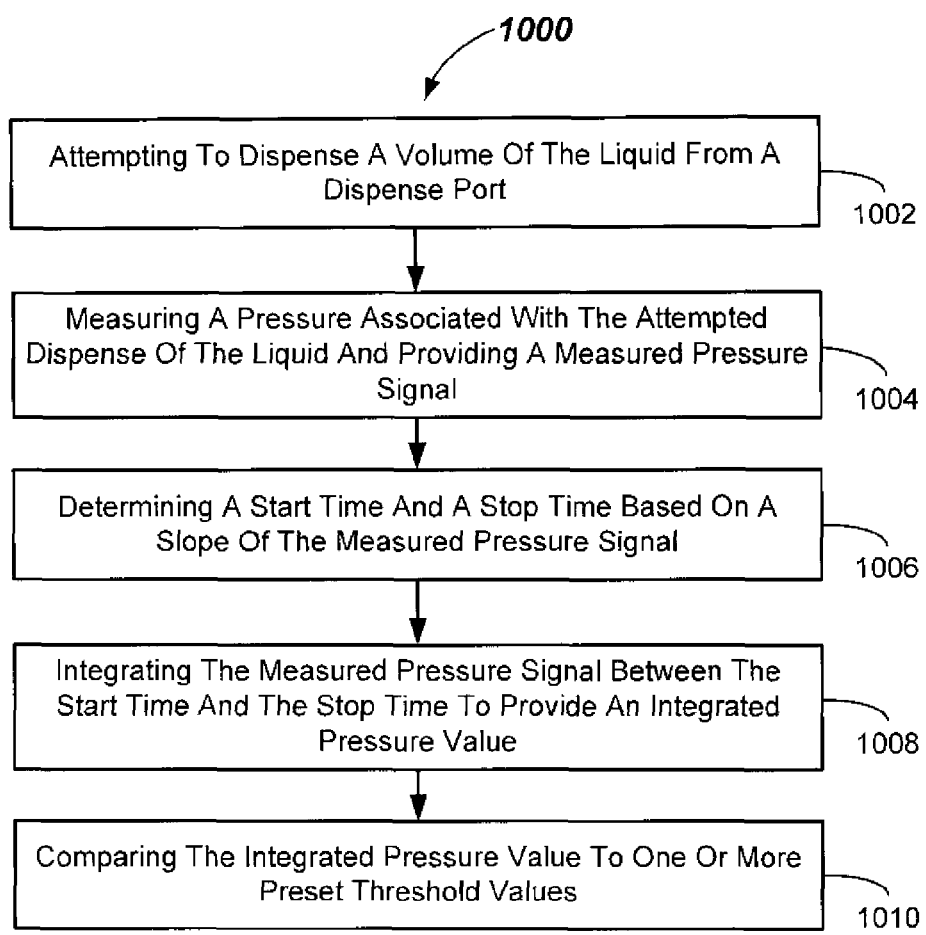
FIG. 10 illustrates a flowchart of a method of detecting pressure during dispensing of a liquid according to embodiments.

FIG. 10 illustrates a flowchart of a method of detecting pressure during dispensing of a liquid, such as the dispensing of an acid or a base. In biological liquid specimen testing, an acid and a base may be added to a reaction vessel 128 following the addition of the specimen and one or more reagents. The method 1000 includes, in 1002, attempting to dispense a volume of the liquid (e.g., an acid or a base) from a dispense port (e.g., dispense port 106). Dispense port 106 may be coupled to a manifold 102 and the dispense port may be located within one liquid dispense shot from the location of the sensor port 112 in the liquid delivery line 107 in some embodiments.

The method 1000 includes measuring a pressure (e.g., a raw measured pressure signal) associated with the attempted dispense of the liquid, and providing a measured pressure signal in 1004. The measured pressure signal may be provided as a normalized signal by having a digitized reference pressure subtracted from the digitized raw measured pressure signal obtained from the pressure sensor 116 in the controller 118. As described above, the reference pressure signal may be determined just before starting the liquid dispense. Normalizing the measured pressure signal may provide an improvement in pressure discrimination by minimizing the effect of pressure signal drift over time.

The method 1000 further includes, in 1006, determining a start time and a stop time based on a slope of the measured pressure signal. As discussed above, the start and stop times are determined as the pressure is sampled continuously. In 1008, the method 1000 includes integrating the measured pressure signal between the start time and the stop time to provide an integrated pressure value.

Once the integrated pressure value is determined, the method 1000 includes, in 1010, comparing the integrated pressure value to one or more preset threshold values. As should be recognized, the method blocks 1006 and 1008 of determining a start time and a stop time based on a slope of the measured pressure signal, and integrating the measured pressure signal between the start time and the stop time to provide an integrated pressure value are may be out substantially simultaneously.

Having shown the preferred embodiments, those skilled in the art will realize many variations are possible that will still be within the scope of the claimed invention. Therefore, it is the intention to limit the invention only as indicated by the scope of the claims.

What is claimed is:

1. A method of detecting pressure during dispensing of a liquid, comprising:
   measuring the pressure of the liquid prior to dispensing the liquid from a dispense port to generate a reference pressure signal;
   dispensing a volume of the liquid from the dispense port;
   measuring the pressure of the liquid over a time period during the dispensing and providing a pressure signal in response to the measuring;
   subtracting the reference pressure signal from the pressure signal to generate a measured pressure signal;
   determining a start time when dispensing starts and a stop time when dispensing stops based on a slope of the measured pressure signal;
   integrating the measured pressure signal between the start time and the stop time to provide an integrated pressure value; and
   comparing the integrated pressure value to one or more preset threshold pressure values.

2. The method of claim 1, comprising:
   performing one or more experimental measurements of the pressure of the liquid during experimental dispensing, and
   determining a predetermined nominal integrated pressure value based on the one or more experimental measurements,
   wherein comparing the integrated pressure value to one or more preset threshold pressure values comprises comparing the integrated pressure value to one or more preset threshold pressure values having a setting of less than the predetermined nominal integrated pressure value.

3. The method of claim 1, wherein comparing the integrated pressure value to one or more preset threshold pressure values comprises:
   performing one or more experimental measurements of the pressure of the liquid during experimental dispensing,
   determining a predetermined nominal integrated pressure value based on the one or more experimental measurements,
   comparing the integrated pressure value to a lower threshold pressure value that is less than the predetermined nominal integrated pressure value, and
   comparing the integrated pressure value to an upper threshold pressure value that is greater than the predetermined nominal integrated pressure value.

4. The method of claim 1, wherein comparing the integrated pressure value to one or more preset threshold pressure values comprises:

performing one or more experimental measurements of the pressure of the liquid during experimental dispensing, determining a predetermined nominal integrated pressure value based on the one or more experimental measurements, and comparing the integrated pressure value to a threshold pressure value that is less than +/−5% from the predetermined nominal integrated pressure value.

5. The method of claim 1, wherein comparing the integrated pressure value to one or more preset threshold pressure values comprises:

performing one or more experimental measurements of the pressure of the liquid during experimental dispensing, determining a predetermined nominal integrated pressure value based on the one or more experimental measurements, and comparing the integrated pressure value to a threshold pressure value that is less than +/−2% from the predetermined nominal integrated pressure value.

6. The method of claim 1, further comprising detecting, in response to the comparing, one or more of:

an air bubble,
a system leak, and
a valve failure.

7. The method of claim 1, further comprising detecting a presence of a blockage in response to the comparing.

8. The method of claim 1, wherein the dispensing the volume of the liquid from the dispense port comprises dispensing one or more of:

an acid; or
a base.

9. The method of claim 1, wherein the dispensing comprises dispensing the liquid into a reaction cuvette.

10. The method of claim 1, wherein the pressure of the liquid is continuously measured during the dispensing.

11. The method of claim 1, wherein if the integrated pressure value is outside the one or more preset threshold pressure values, then one of:

an alert is indicated; and
the dispensing is stopped.

12. The method of claim 1, wherein the start time is determined by estimating a slope of the measured pressure signal, and wherein the start time occurs when the estimated slope exceeds a start threshold pressure value.

13. The method of claim 1, wherein the stop time is determined by estimating a slope of the measured pressure signal, and wherein the stop time occurs when the estimated slope exceeds a stop threshold pressure value.

14. The method of claim 1, comprising:

determining a first measured pressure signal of the liquid being dispensed at a beginning of a time window;

determining a second measured pressure signal of the liquid being dispensed at an end of the time window;

determining a difference between the first measured pressure signal and the second measured pressure signal; and determining the start time of the dispensing as occurring when the difference between the first measured pressure signal and the second measured pressure signal exceeds a start threshold pressure signal value.

15. The method of claim 1, comprising:

determining a first measured pressure signal of the liquid being dispensed at a beginning of a time window;

determining a second measured pressure signal of the liquid being dispensed at an end of the time window;

determining a difference between the first measured pressure signal and the second measured pressure signal; and determining the stop time of the dispensing as occurring when the difference between the first measured pressure signal and the second measured pressure signal exceeds a stop threshold pressure signal value.

* * * * *